United States Patent [19]

Briggs

[11] Patent Number: 4,486,923
[45] Date of Patent: Dec. 11, 1984

[54] CLOSURE DEVICE FOR BAGS OR POUCHES

[75] Inventor: Peter J. Briggs, Sompting, England

[73] Assignee: Matburn (Holdings) Limited, London, England

[21] Appl. No.: 71,474

[22] Filed: Aug. 31, 1979

[30] Foreign Application Priority Data

Sep. 7, 1978 [GB] United Kingdom ............... 35902/78
Apr. 19, 1979 [GB] United Kingdom ................. 7913729

[51] Int. Cl.³ .............................................. B65D 77/10
[52] U.S. Cl. .................................. 24/30.5 R; 383/68
[58] Field of Search ............... 24/30.5, 243 R, 245 A, 24/246, 255 R, 255 SL; 229/62, 65

[56] References Cited

U.S. PATENT DOCUMENTS

| | | | |
|---|---|---|---|
| T983,001 | 6/1979 | Coffey | 24/30.5 R X |
| 1,277,327 | 8/1918 | Lundqvist | 24/30.5 R |
| 2,030,634 | 2/1936 | Holloway | 229/65 X |
| 3,112,542 | 12/1963 | Brunson | 24/30.5 R |
| 3,384,938 | 5/1968 | O'Connor | 24/255 R X |
| 3,512,227 | 5/1970 | Krawagna | 24/243 R |
| 3,621,539 | 11/1971 | Ayers | 24/30.5 R |
| 3,818,553 | 6/1974 | Parmenter | 24/30.5 R |

*Primary Examiner*—Francis K. Zugel
*Assistant Examiner*—Peter A. Aschenbrenner
*Attorney, Agent, or Firm*—McAulay, Fields, Fisher, Goldstein & Nissen

[57] ABSTRACT

A closure device for a surgical post-operative drainage bag comprises a first panel which is curved and a second panel. The two panels are joined by a hinged connection. The second panel comprises two strip-like portions joined together by an intermediate hinge. When the device is closed, the free edge of the second panel tightly engages within the inside of the lip so as to be placed in a stressed condition and so that a portion of the bag positioned between the inside of the lip and the free edge of the second panel may be secured.

4 Claims, 5 Drawing Figures

CLOSURE DEVICE FOR BAGS OR POUCHES

BACKGROUND TO INVENTION

Surgical post-operative drainage bags such as colostomy or ileostomy bags (often called "ostomy bags") are usually made of flexible plastics material. They frequently have an outlet at what is the bottom of the bag when the bag is in use. Such an outlet must have an effective closure which is preferably simple to operate. An object of the invention is to provide a simple and effective closure device for such bags.

BRIEF SUMMARY OF THE INVENTION

According to the invention, a closure device for a bag or pouch comprises first and second panels with a hinged connection between adjacent edges of the panels, the first panel having a lip at an edge remote from the hinged connection and the second panel having a free edge which, when the device is in a closed position, can tightly engage within the inside of the lip thereby to place the second panel in a stressed condition so a portion of the bag or pouch positioned between the inside of the lip and the free edge of the second panel may be secured. Both panels may be of flexible plastics material and the first panel may be curved to present a concave face, the lip entering on the concave side and the second panel may have a dimension between the hinged connection and its free edge which is greater than the distance between the hinged connection and the lip of the first panel. The distance around the curve of the curved first panel must not be greater and may be slightly smaller, than the distance between the hinged connection and the free edge of the second panel.

If desired, the closure device may have a flexible strap extending from one end of one of the panels and removably fastened to a fastener at the other end of the same panel. In another alternative, the second panel may have a third or extension panel extending beyond its free edge.

The second panel may have an intermediate hinge parallel to the hinged connection with the first panel and the second panel movable about its hinges between an open position in which the intermediate hinge is remote from the first panel and the closed position in which the intermediate hinge is adjacent the first panel and the free edge of the second panel is engaged within the lip of the first panel.

The invention also provides a surgical post-operative drainage bag or pouch having such a closure.

BRIEF DESCRIPTION OF ACCOMPANYING DRAWINGS

DESCRIPTION OF SOME EMBODIMENTS

Figure 1:
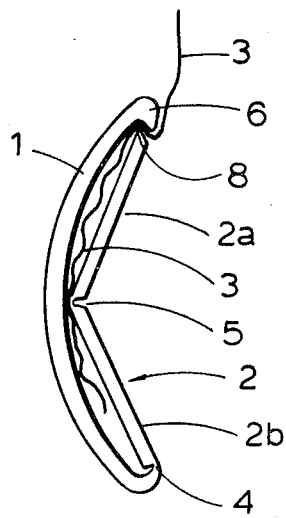
FIG. 1 is an end view of a closure clip in its closed position.
Figure 2:
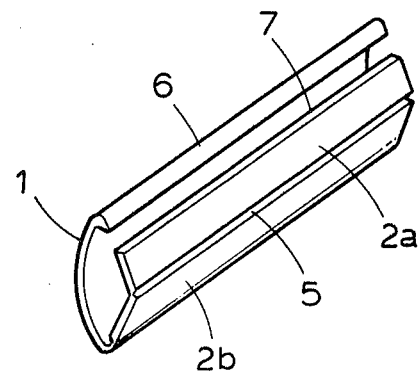
FIG. 2 is a perspective view of the closure clip in an open position.

FIGS. 1 and 2 of the drawings illustrate a closure clip for an outlet of a colostomy bag. The clip is formed in one piece from a flexible plastics material such as polypropylene. The clip comprises a first panel 1 which is curved to present convex and concave surfaces and a second panel 2. A surgical post-operative drainage bag 3, is, as shown in FIG. 1, retained between the two panels when they are closed together.

The panel 2 is joined to the first panel 1 by a hinged connection 4. The second panel 2 comprises two strip-like portions 2a and 2b joined together by an intermediate hinge 5.

The first panel 1 has a lip 6 on its concave side and at its free edge, i.e. the edge remote from the hinged connection 4.

When the clip is in the open position shown in FIG. 2, the free edge 7 of the panel portion 2a is clear of the lip 6 of the first panel. It will be appreciated that when the clip is open and the two panels 2a and 2b lie in a single plane, the distance between the hinged connection 4 and the free edge 7 of the panel 2 is greater than the distance between the hinged connection 4 and inside of the lip 6 of the first panel 1. The panel 2 is then, of course, in an unstressed condition. In order to engage the free edge 7 of the panel 2 inside the lip 6 of the panel 1, it is necessary to incline the panel portions 2a and 2b relatively to one another so that the hinged connection 5 between the two panel portions is remote from the first panel 1 as shown in FIG. 2.

When it is desired to close a bag, the sheeting of the bag is arranged adjacent the inside of the first panel 1 and the second panel 2 is closed onto the first panel so that the free edge 7 of the second panel is arranged beneath the lip 6. Pressure is then applied on the panel 2, conveniently at the hinge 5, to cause it to snap over to a closed position as shown in FIG. 1. The relative dimensions of the first panel 1 and the second panel 2 are such that when the panels are in the closed position shown in FIG. 1, the free edge 7 of the panel 2 makes tight contact with, and presses against, the inside of the lip 6, along a line indicated at 8 in FIG. 1. In this position, the panel 2 is in a stressed condition and the bag 3 is held between the two panels so that the bag will be sealed along the line 8 between the free edge 7 of the panel 2a and the inside of the lip 6.

To open the clip and release the bag, pressure is applied to reverse the relative inclination between the two portions 2a and 2b of the second panel 2 so that they revert to a position similar to that illustrated in FIG. 2. The free edge 7 of the second panel may then be disengaged from the inside of the lip 6. If desired, apertures can be provided in the curved first panel 1 through which pressure may be directly applied to the panel 2 in order to open the clip. For example, the ends of the curved first panel 1 can be provided with recesses through which pressure can be applied to the panel 2. If desired protuberances accessible through the apertures or recesses can be provided to assist in applying pressure to the panel 2.

In a modification (not illustrated) an integral strap of the same material as the first and second panels 1, 2 extends outwardly from one end of one of the panels. A fastener is provided on the other end of the same panel and the free end of the strap may be removably secured to this fastener. In use, the bag will lie between the clip and the strap, thereby improving the general "lie" of the clip on the bag.

Figure 3:
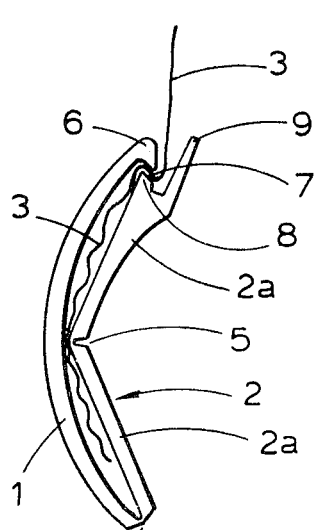
FIG. 3 is an end view of a modified clip.
Figure 5:
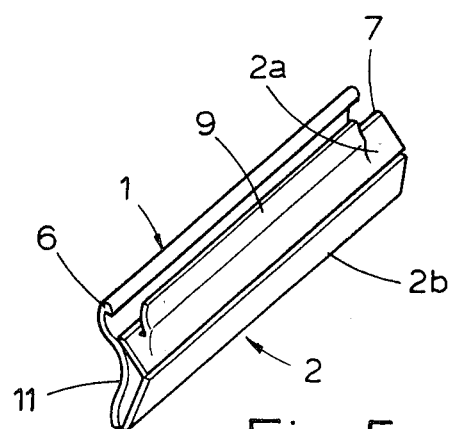
FIGS. 4 and 5 are respectively a plan view and a perspective view of the clip illustrated in FIG. 3.
Figure 4:
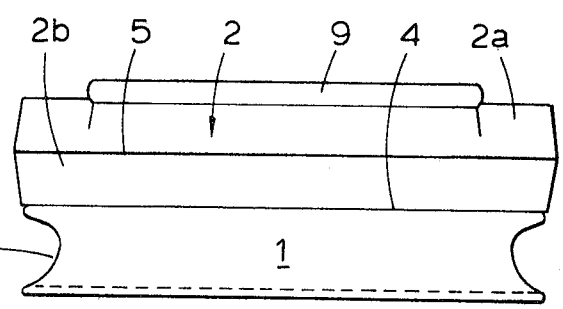

In another modification illustrated in FIGS. 3, 4 and 5 a third or extension panel 9 extends beyond, and is offset from, the free edge 7 of the second panel 2. As in the embodiment of FIGS. 1 and 2 this free edge of the panel can engage inside the lip 6 of the first panel 1, the panel 9 being positioned outside the lip 6. This extension panel 9 improves the "lie" of the bag when the device is in use and makes it easier to arrange the device in a position acceptably comfortable to the patient. In this modification, the ends of the first panel are recessed or curved concavely at 11 to give access to portions of the second panel in order that pressure may be applied easily to the panel 2 when it is desired to release the panel 2 from the panel 1.

What is claimed is:

1. A closure device operable between an open and a closed position for sealing a bag or a pouch comprising a first panel, a second flexible panel, a hinged connection between adjacent edges of said two panels, a lip at an end of said first panel in facing relationship to said hinged connection, a free end on said second panel opposite said hinged connection, said second panel having a dimension between said hinged connection and said free end which is greater than the distance between said hinged connection and the inside of said lip, said free end adapted to be received in tight abutting engagement with the inside of said lip when said closure device is moved to the closed position whereby said second panel is placed under stress, by reversing the position of its center relative to its ends, wherein said second panel has an intermediate hinge parallel to said hinged connection with said first panel and said second panel is movable about said hinges between an open position in which said intermediate hinge is remote from said concave face of said first panel and a closed position in which said intermediate hinge is adjacent said concave face of said first panel and said free edge of said second panel is engaged within said lip of said first panel, so that a portion of the bag or pouch positioned between the inside of said lip and said free edge of said second panel is sealed by the force exerted by said second panel against the inside of said lip.

2. A closure device as claimed in claim 1, wherein both of said panels are of flexible plastic material, said first panel being curved to present a concave face, and said lip extending on the concave side of said panel.

3. A closure device as claimed in claim 1, wherein said second panel has an extension panel offset from, and extending beyond, said free edge of said second panel; said extension panel being positioned outside said lip of said first panel when said free edge of said second panel is engaged inside said lip.

4. A closure device as claimed in claim 1, wherein said first panel has ends which are recessed to give access to portions of said second panel thereby to permit pressure easily to be applied to said second panel when it is desired to release said second panel from said first panel.

* * * * *